US009259315B2

(12) United States Patent
Zhou et al.

(10) Patent No.: US 9,259,315 B2
(45) Date of Patent: Feb. 16, 2016

(54) LOW PROFILE HEART VALVE DELIVERY SYSTEM AND METHOD

(71) Applicant: Boston Scientific Scimed, Inc., Maple Grove, MN (US)

(72) Inventors: Pu Zhou, Maple Grove, MN (US); Huisun Wang, Maple Grove, MN (US); James Q. Feng, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 22 days.

(21) Appl. No.: 13/939,534

(22) Filed: Jul. 11, 2013

(65) Prior Publication Data

US 2014/0018911 A1  Jan. 16, 2014

Related U.S. Application Data

(60) Provisional application No. 61/670,776, filed on Jul. 12, 2012.

(51) Int. Cl.
*A61F 2/24* (2006.01)
*A61F 2/966* (2013.01)

(52) U.S. Cl.
CPC ............. *A61F 2/2427* (2013.01); *A61F 2/2436* (2013.01); *A61F 2/966* (2013.01)

(58) Field of Classification Search
CPC ...... A61F 2/2436; A61F 2/966; A61F 2/2427
USPC ................................................ 623/1.35, 2.11
See application file for complete search history.

(56) References Cited

U.S. PATENT DOCUMENTS

| 6,099,548 | A  | * | 8/2000 | Taheri .......................... 606/198 |
| 6,413,274 | B1 | * | 7/2002 | Pedros ......................... 623/2.11 |
| 6,425,916 | B1 | * | 7/2002 | Garrison et al. ............. 623/2.11 |
| 7,416,557 | B2 |   | 8/2008 | Drasler et al. |
| 2005/0137688 | A1 |   | 6/2005 | Salahieh et al. |
| 2007/0016288 | A1 | * | 1/2007 | Gurskis et al. .............. 623/2.11 |
| 2007/0112425 | A1 | * | 5/2007 | Schaller et al. ............. 623/2.37 |
| 2007/0233237 | A1 | * | 10/2007 | Krivoruchko ............... 623/2.11 |
| 2008/0033543 | A1 | * | 2/2008 | Gurskis et al. .............. 623/2.11 |
| 2008/0319526 | A1 | * | 12/2008 | Hill et al. .................... 623/1.12 |

FOREIGN PATENT DOCUMENTS

| WO | 0047139 | 8/2000 |
| WO | 2005062980 | 7/2005 |
| WO | 2007009117 | 1/2007 |

OTHER PUBLICATIONS

Notification of Transmittal of the International Search Report and the Written Opinion of the International Searching Authority; or the Declaration for PCT/20131050087, mailed on Oct. 16, 2013.

* cited by examiner

*Primary Examiner* — Richard Louis
(74) *Attorney, Agent, or Firm* — Seager, Tufte & Wickhem LLP

(57) ABSTRACT

A heart valve delivery system includes a low-profile catheter having an outer sheath, the outer sheath having therein a stent and a replacement heart valve. In an unemployed configuration, the stent is located distally to the replacement heart valve. Upon deployment, however, the stent and replacement heart valve are expanded and the replacement heart valve is situated within the stent.

8 Claims, 6 Drawing Sheets

LOW PROFILE HEART VALVE DELIVERY SYSTEM AND METHOD

CROSS-REFERENCE TO RELATED APPLICATIONS

This Application claims the benefit of and priority to U.S. Provisional Application No. 61/670,776, filed Jul. 12, 2012, the entire contents of which are herein incorporated by reference.

STATEMENT REGARDING FEDERALLY SPONSORED RESEARCH

Not Applicable.

BACKGROUND OF THE INVENTION

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

Various forms of replacement heart valves are known in the art. Moreover, a variety of catheter systems have been developed to implant such replacement heart valves. One method of implantation is Transcatheter Aortic-Valve Implantation (TAVI). Existing TAVI systems suffer from a number of deficiencies, however. In particular, known TAVI systems are relatively large in diameter, which can impede insertion of the catheter. Further, known TAVI systems suffer from a lack of flexibility, which results from the large size of known TAVI systems. Additionally, the large size requires a large entrance incision, further complicating the procedure and increasing risk to the patient.

In light of the foregoing drawbacks associated with existing TAVI systems, there remains a need for a TAVI system having a smaller profile and greater flexibility.

BRIEF SUMMARY OF THE INVENTION

In some embodiments, a percutaneous heart valve delivery system has a first configuration and a second configuration. In some embodiments, the system comprises a sheath, a stent, a replacement valve, and at least one suture line. In some embodiments, the replacement valve and stent each have respective proximal ends and distal ends. In some embodiments, the at least one suture line extends between the stent and the replacement valve. In some embodiments, when the system is in the first configuration, the stent and replacement valve are disposed within the sheath and the distal end of the replacement valve is proximal to the proximal end of the stent. Further, in some embodiments, when the system is in the second configuration, the distal end of the replacement valve is distal to the proximal end of the stent.

BRIEF DESCRIPTION OF THE SEVERAL VIEWS OF THE DRAWING(S)

Figure 4:
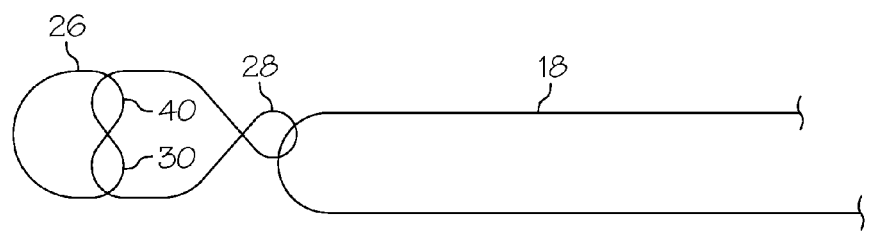

FIG. 4 shows an embodiment of the pull line 18 and suture 26 of the heart valve delivery system 10.

Figure 5:
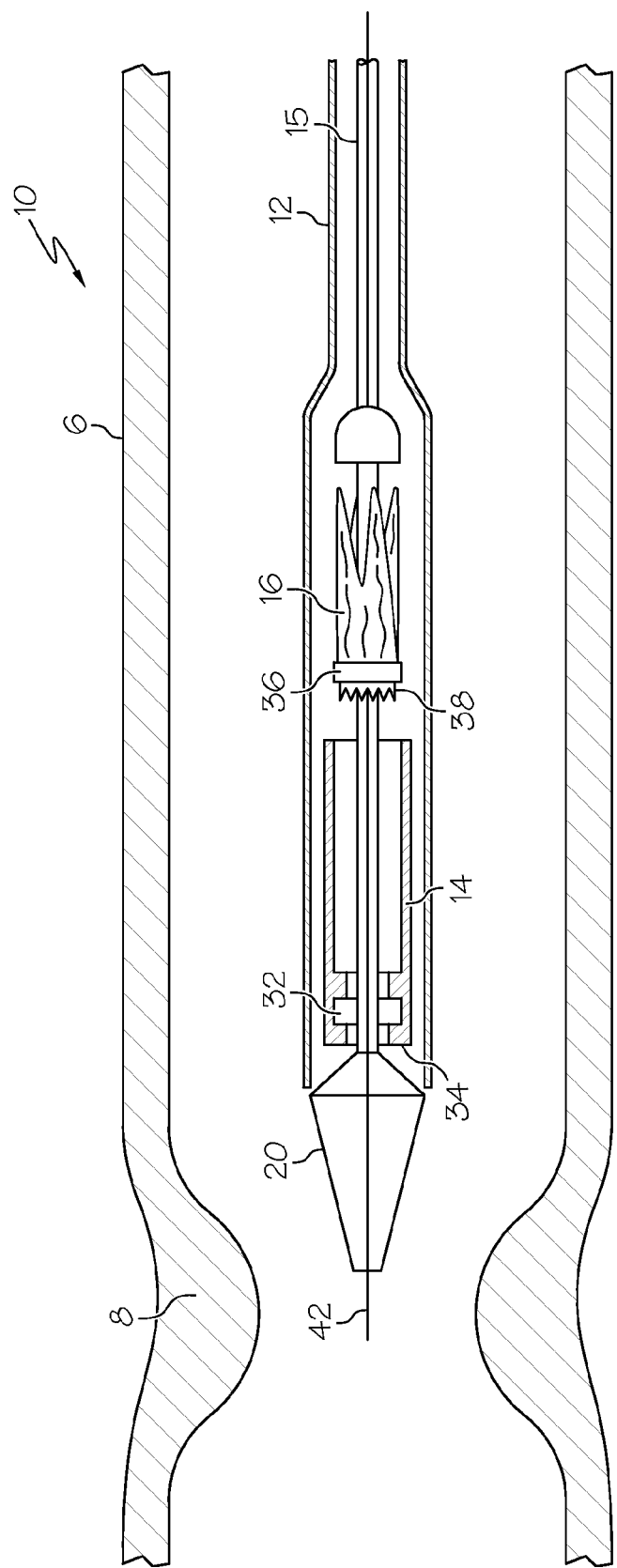

FIG. 5 shows a cutaway view of a portion of an embodiment of the heart valve delivery system 10 prior to deployment.

Figure 6:
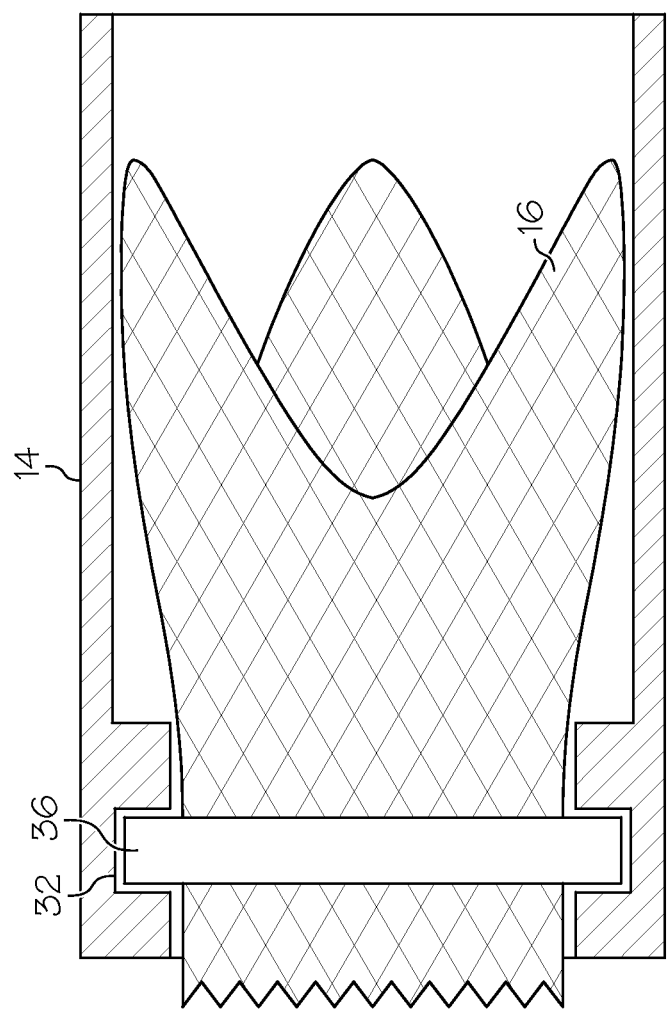

FIG. 6 shows the stent 14 and replacement valve 16 of FIG. 5 after deployment thereof.

DETAILED DESCRIPTION OF THE INVENTION

While this invention may be embodied in many different forms, there are described herein specific embodiments. This description is an exemplification of the principles of the invention and is not intended to limit it to the particular embodiments illustrated.

For the purposes of this disclosure, like reference numerals in the figures shall refer to like features unless otherwise indicated.

Figure 1:
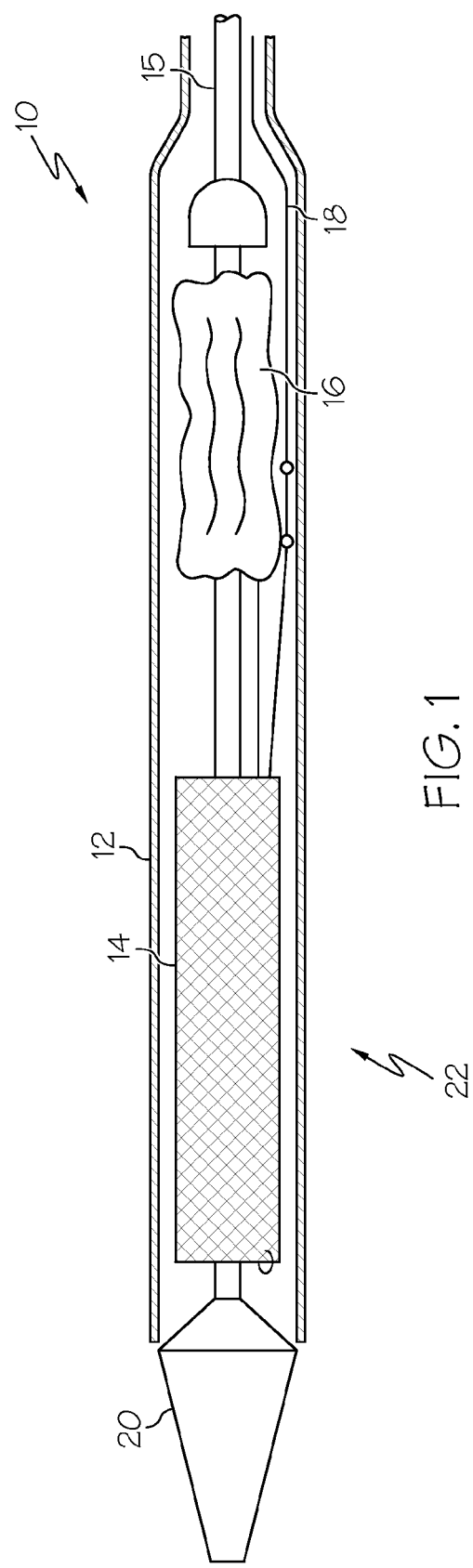
FIG. 1 shows a partial cutaway view of a portion of an embodiment of the heart valve delivery system 10.

In some embodiments, for example as shown in FIG. 1, a heart valve delivery system 10 comprises a sheath 12, a stent 14, a replacement valve 16, and an inner tubular member 15. In some embodiments, the heart valve delivery system 10 further comprises at least one pull line 18. Additionally, in some embodiments, the heart valve delivery system 10 further comprises a nosecone 20. In some embodiments, the nosecone 20 is attached to the inner tubular member 15, for example via an overmolding process. In some embodiments, the heart valve delivery system 10 is designed for percutaneous implantation.

The heart valve delivery system 10 has a delivery configuration 22 (FIG. 1) wherein, in some embodiments, the stent 14 is disposed distally to the replacement valve 16 within the sheath 12. In this way, in some embodiments, the stent 14 and replacement valve 16 are longitudinally spaced apart from one another along the length of the sheath 12 when in the delivery configuration 22. Placement of the stent 14 and replacement heart valve 16 in a non-overlapping fashion, while in the sheath 12, allows the heart valve delivery system 10 to be smaller and more flexible than known TAVI systems. In some embodiments, the stent 14 is deployed from the sheath 12 prior to deployment of the replacement valve 16. Moreover, in some embodiments, the replacement heart valve 16 is tightly wrapped into a cylindrical shape within the sheath 12.

Figure 2:
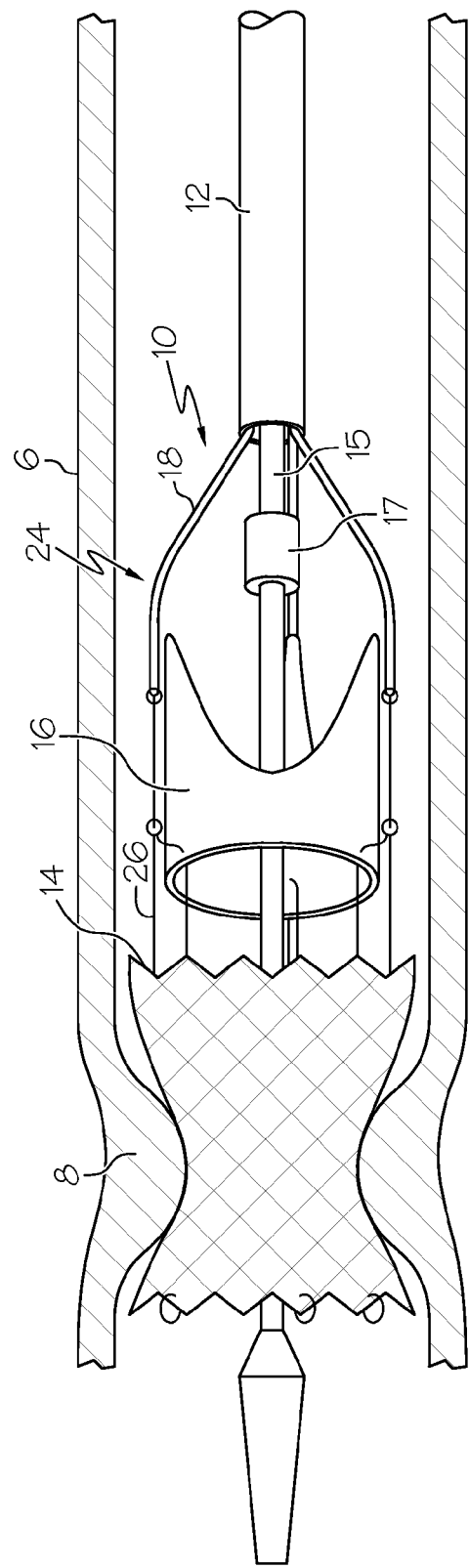
FIG. 2 shows a cutaway view of a portion of the embodiment of FIG. 1 in a partially deployed configuration 24.

With regard to FIG. 2, the heart valve delivery system 10 is shown in a partially deployed configuration 24 within the ascending aorta 6 and aortic valve 8. As illustrated in FIG. 2, the stent 14 and replacement heart valve 16 have been deployed from the sheath 12. In particular, in some embodiments, the stent 14 is deployed from the sheath 12 and expanded, prior to deployment of the replacement heart valve 16. In order to facilitate deployment and expansion of the stent 14 and replacement heart valve 16, in some embodiments, the heart valve delivery assembly 10 comprises at least one suture line 26 extending between the stent 14 and the replacement heart valve 16. Moreover, in some embodiments, the heart valve delivery system 10 comprises a pusher 17, which can help facilitate deployment of the replacement valve 16.

Figure 3A:
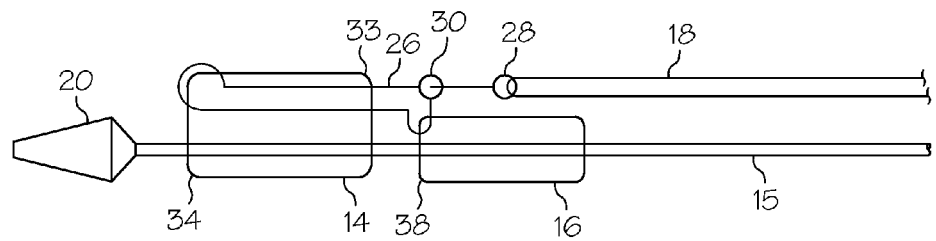
FIGS. 3A-3E show schematic views of the heart valve delivery system 10 in various stages of deployment.

In some embodiments, the suture line 26 is used to secure the replacement valve 16 to the stent 14. As schematically shown in FIG. 3A, the stent 14 and the replacement valve 16 are in an unexpanded configuration, for example as they would be disposed within a sheath 12 (not shown) for introduction into a body lumen. The unexpanded configuration is alternatively referred to herein as a first configuration. As further shown in FIG. 3A, in some embodiments, the pull line 18 extends through a first loop 28 and is doubled-back on itself. Further, the pull line 18 extends proximally to the proximal end of the sheath 12 (FIG. 1) so that the pull line 18 can be manipulated by the operator.

With further regard to FIG. 3A, in some embodiments, the suture line 26 is attached to the first loop 28. The suture line 26 extends distally from the first loop 28 through a second loop 30, a portion of the replacement valve 16, and the stent 14. In some embodiments, a segment of the suture line 26 is formed into the second loop 30 in a slip-knot or similar knot that tightens on itself. In some embodiments, the suture line 26, or a portion thereof, is formed from a bioabsorbable material. In some embodiments, the bioabsorbable material comprises or consists of hydro polymers, hydro gels, collagen, or suitable combinations thereof. In some embodiments, the bioabsorbable material includes poly(lactic-co-glycolic acid) (PLGA) or poly(lactic acid) (PLA), for example.

As further shown in FIG. 3A, the stent 14 has a proximal end 33 and a distal end 34. In some embodiments, prior to deployment, the proximal end 33 of the stent 14 is located distally to the distal end 38 of the replacement valve 16. Stated differently, in some embodiments, the distal end 38 of the replacement valve 16 is proximal to the proximal end 33 of the stent 14.

Figure 3B:
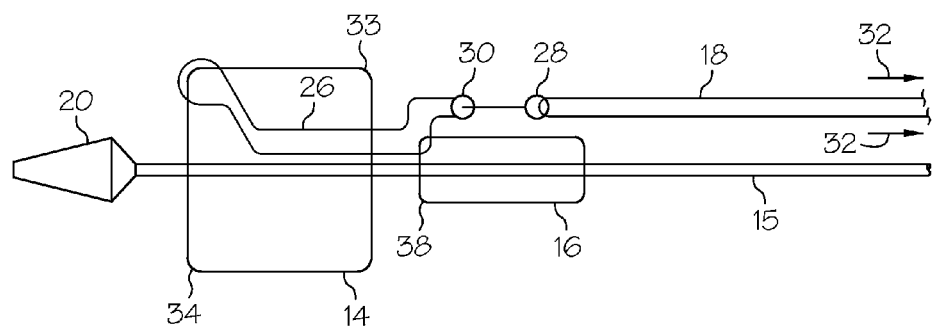

Turning to FIG. 3B, in order to facilitate deployment of the stent 14 and replacement valve 16, the stent 14 is first deployed, for example via a sheath 12, and expanded against an aortic valve, as shown in FIG. 2. Thereafter, the operator pulls on the pull line 18. In particular, in some embodiments, the operator pulls both ends of the pull line, as illustrated via arrows 32. In this way, the replacement valve 16 is moved distally toward the stent 14.

Figure 3C:
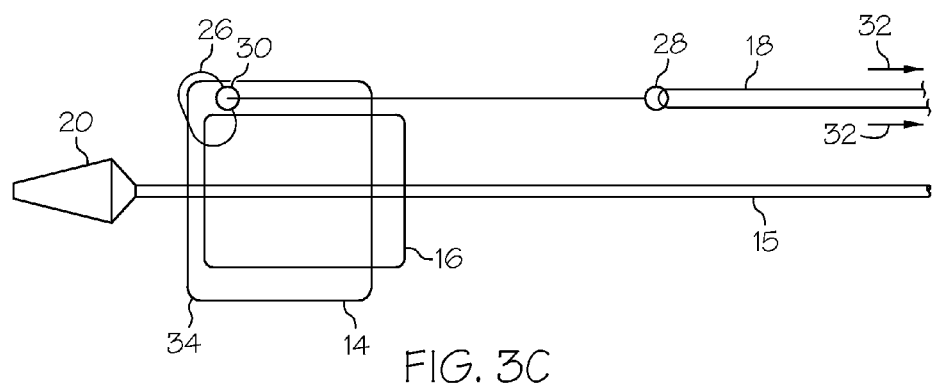

With regard to FIG. 3C, pulling the pull line 18 further moves the replacement valve 16 distally until the replacement valve 16 is situated within the stent 14. In some embodiments, as the replacement valve 16 is moved into position within the stent 14, the replacement valve 16 is first partially expanded, then it is situated within the stent 14 and, finally, it is fully expanded and anchored to the stent 14 via suture line 26. In some embodiments, the replacement valve 16 is moved into position within the stent 14 while in an unexpanded configuration and subsequently expanded. Further, in some embodiments, the replacement valve 16 is fully expanded and then moved into position within the stent 14. In some embodiments, the replacement valve 16 is expanded within the stent 14 by pulling on the suture line 26. Pulling of the suture line 26 thereby moves the replacement valve 16 longitudinally to position within the stent 14 and also expands the replacement valve 16 in a radial direction.

Figure 3D:
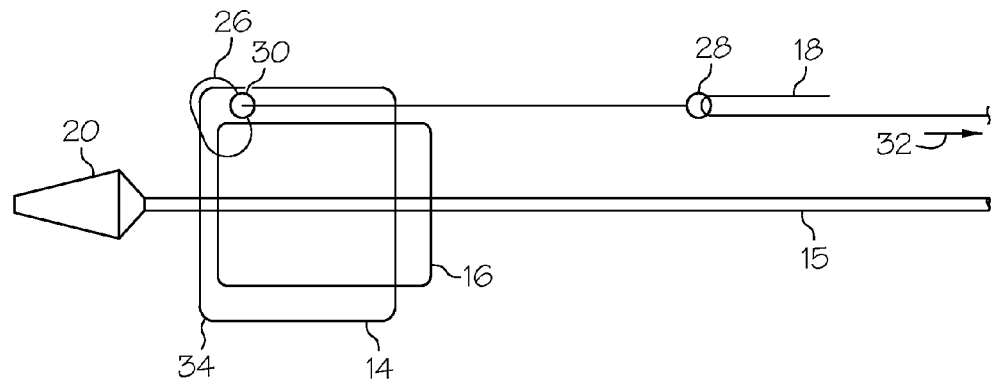

As shown in FIG. 3D, in some embodiments, after the replacement valve 16 is disposed within the stent 14, one end of the pull line 18 is released and the operator pulls on the other end, as illustrated via arrow 32 in FIG. 3D. In this way, the pull line 18 is removed from the patient's body, leaving the stent 14, the replacement valve 16, and the suture line 26—which, in the illustrated embodiment, forms the second loop 30.

Figure 3E:
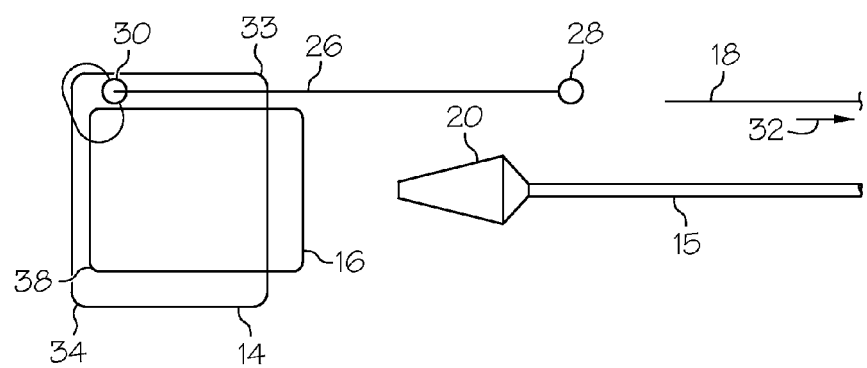

With regard to FIG. 3E, in some embodiments, and upon deployment, the heart valve delivery system 10 is in a second configuration wherein the distal end 38 of the replacement valve 16 is distal to the proximal end 33 of the stent 14. Further, the delivery system 10 is removed from the patient's body.

In some embodiments, the suture line 26 extends through a distal end 34 of the stent 14 and a distal end 38 of the replacement valve 16. Moreover, in some embodiments, the suture line 26 is routed through holes or slots in the stent 14. In some embodiments, the suture line 26 is routed between struts. It is also contemplated that the suture line 26 is anchored or tied to the struts, holes, slots, or other features on the stent 14.

In some embodiments, the replacement valve 16 has one or more reinforced areas through which the suture line 26 can be routed. In some embodiments, the reinforced areas are sections of harder or more rigid material. In some embodiments, the suture line 26 is attached to such reinforced areas.

Although illustrated in FIGS. 3A-3E with only a single suture line 26, it will be appreciated that, in some embodiments, the heart valve delivery assembly 10 comprises six to twenty suture lines 26. In some embodiments, the heart valve delivery assembly 10 has 8, 10, 12, or 14 suture lines 26.

In some embodiments, the stent 14 comprises a skirt disposed at a distal end 34 thereof. In some embodiments, the skirt provides a seal between the stent 14 and the adjacent tissue of the aortic valve 8, upon implantation of the stent 14. In some embodiments, the suture line 26 is routed through a portion of the skirt.

In some embodiments, the replacement valve 16 comprises an expandable frame. In some embodiments, the expandable frame comprises a shape-memory material, for example a nickel-titanium alloy. Other suitable material can also be used.

Further, in some embodiments, the replacement valve 16 is expanded by way of suture line 26. In particular, in some embodiments, as the pull line 18 is pulled by the operator, the suture line 26 tightens and expands the replacement valve 16. In some embodiments, the replacement valve 16 is expanded without a self-expanding frame.

With regard to FIG. 4, an embodiment of the suture line 26 and pull line 18 is shown. In the embodiment of FIG. 4, the suture line 26 forms the first loop 28 and second loop 30. In some embodiments, the suture line 26 forms a plurality of twists 40 to form a plurality of loops, which facilitate tightening of the suture line 26, as desired.

Turning to FIG. 5, an embodiment of the heart valve delivery assembly 10 is shown therein. In the embodiment of FIG. 5, the stent 14 and replacement valve 16 are longitudinally offset from one another while in the sheath 12. Further, the stent 14 is deployed prior to deployment of the replacement valve 16.

In some embodiments, for example as shown in FIG. 5, the stent has a locking slot 32. In some embodiments, the locking slot 32 is disposed at or near the distal end 34 of the stent 14. Further, in some embodiments, the replacement valve 16 has a protruding member 36 which, in some embodients, is disposed at or near the distal end 38 of the replacement valve 16. In some embodiments, the locking slot 32 is annularly shaped. Further, in some embodiments, the protruding member 36 is annularly shaped to mate with the locking slot 32.

As shown in FIG. 6, upon deployment of the stent 14 and replacement valve 16, the protruding member 36 locks into place within the locking slot 32, thereby securing the replacement valve 16 within the stent 14. It will appreciated that the replacement valve 16 and stent 14 can include any suitable arrangement of locking mechanism. For example, in some embodiments, the replacement valve 16 has a locking slot while the stent 14 has a protruding member 36. Other suitable mechanisms and arrangements are also permissible.

In some embodiments, the stent 14 and replacement valve 16 are deployed by first deploying the stent 14 from the sheath 12 (FIG. 5). Upon release of the stent 14 from the sheath 12, the stent 14 can be self-expanded or it can be expanded via a balloon. Once the stent 14 is expanded at a desired location within the aortic valve 8, the sheath 12 is adjusted for placement of the replacement valve 16 within the stent 14. Subsequently, the replacement valve 16 is deployed from the sheath 12. In some embodiments, the replacement valve 16 partially expands within the stent 14 but it is still movable longitudinally within the stent 14. In this way, the replacement valve 16 is moved, as necessary, until the protruding member 36 locks into place within the locking slot 32. In some embodiments, the replacement valve 16 is self-expandable.

It will be appreciated that the heart valve delivery system 10 is not limited to use as a TAVI device. The heart valve delivery system 10 can also be used for the replacement of other heart valves.

In some embodiments, the sheath 12, having a stent 14 and replacement valve 16, has a diameter less than 14 French. In some embodiments, the sheath 12, having a stent 14 and replacement valve 16, has a diameter between 14 and 18 French.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A percutaneous heart valve delivery system having a first configuration and a second configuration, the system comprising:
   a sheath;
   a stent having a proximal end, a distal end, and a lateral side;
   a replacement valve having a proximal end, a distal end, and a lateral side;
   at least one suture line extending through the lateral side of the replacement valve, the lateral side of the stent, and between the stent and replacement valve;
   wherein, when the system is in the first configuration, the stent and replacement valve are disposed within the sheath and the distal end of the replacement valve is proximal to the proximal end of the stent; and
   when the system is in the second configuration, the distal end of the replacement valve is distal to the proximal end of the stent;
   wherein pulling proximally on the at least one suture line shifts the system from the first configuration to the second configuration by translating the replacement valve distally toward the stent.

2. The system of claim 1, wherein the stent is self-expanding.

3. The system of claim 1, wherein the replacement heart valve is self-expanding.

4. The system of claim 1 further comprising at least one pull line, wherein the sheath has a proximal end and a distal end and the at least one pull line extends beyond the proximal end of the sheath.

5. The system of claim 1, wherein the at least one suture line comprises between six and twenty suture lines.

6. The system of claim 5 further comprising a plurality of pull lines, each of the pull lines connected to one of the suture lines when the system is in a first configuration.

7. The system of claim 1, wherein at least a portion of the at least one suture line comprises a bioabsorbable material.

8. A method of deploying a replacement heart valve comprising: providing a percutaneous heart valve delivery system comprising: a sheath; a stent having a lateral side; a replacement heart valve having a lateral side; and at least one suture line routed through the lateral side of the replacement heart valve and the lateral side of the stent; inserting the heart valve delivery system through a body lumen; deploying the stent from the sheath; expanding the stent; deploying the replacement heart valve from the sheath; and pulling proximally on the at least one suture line to radially expand the replacement heart valve and move distally the replacement heart valve into contact with the stent.

* * * * *